(12) United States Patent
Johnson et al.

(10) Patent No.: US 10,254,240 B2
(45) Date of Patent: Apr. 9, 2019

(54) PULSED WAVE GUIDE LIQUID QUALITY MEASUREMENT

(71) Applicant: LITTELFUSE, INC., Chicago, IL (US)

(72) Inventors: Brian Johnson, Saltash (GB); Efrem Fesshaie, Norwich (GB); Rimantas Misevicius, Kaunas (LT)

(73) Assignee: LITTELFUSE, INC., Chicago, IL (US)

( * ) Notice: Subject to any disclaimer, the term of this patent is extended or adjusted under 35 U.S.C. 154(b) by 522 days.

(21) Appl. No.: 14/740,785

(22) Filed: Jun. 16, 2015

(65) Prior Publication Data

US 2015/0362447 A1 Dec. 17, 2015

Related U.S. Application Data

(60) Provisional application No. 62/013,037, filed on Jun. 17, 2014.

(51) Int. Cl.
*H04B 3/52* (2006.01)
*H01P 3/00* (2006.01)
*G01N 27/02* (2006.01)

(52) U.S. Cl.
CPC .............................. *G01N 27/025* (2013.01)

(58) Field of Classification Search
CPC ........ G01F 23/284; G01F 23/26; G01F 23/28; G01F 25/0061; A61B 8/06; H04B 3/52; H01P 3/00; H01P 3/10
See application file for complete search history.

(56) References Cited

U.S. PATENT DOCUMENTS

| | | | | |
|---|---|---|---|---|
| 2,983,839 | A | * 5/1961 | Field | H03J 7/32 313/453 |
| 4,335,613 | A | * 6/1982 | Luukkala | G01N 29/11 340/582 |
| 5,174,295 | A | * 12/1992 | Christian | A61B 8/06 600/468 |
| 5,819,582 | A | * 10/1998 | Kelly | G01F 23/2845 324/642 |

* cited by examiner

*Primary Examiner* — Alesa Allgood

(57) ABSTRACT

A waveguide system may include an inner core, and a conductor wound around the inner core in conductive coils having a coil length, wherein a voltage pulse received by the pulsed waveguide propagates as an induced wave having a group velocity, the group velocity being below a threshold velocity, wherein a reflection signal or an end of line signal generated within the conductor from the induced wave is detectable from the initial voltage pulse.

11 Claims, 8 Drawing Sheets

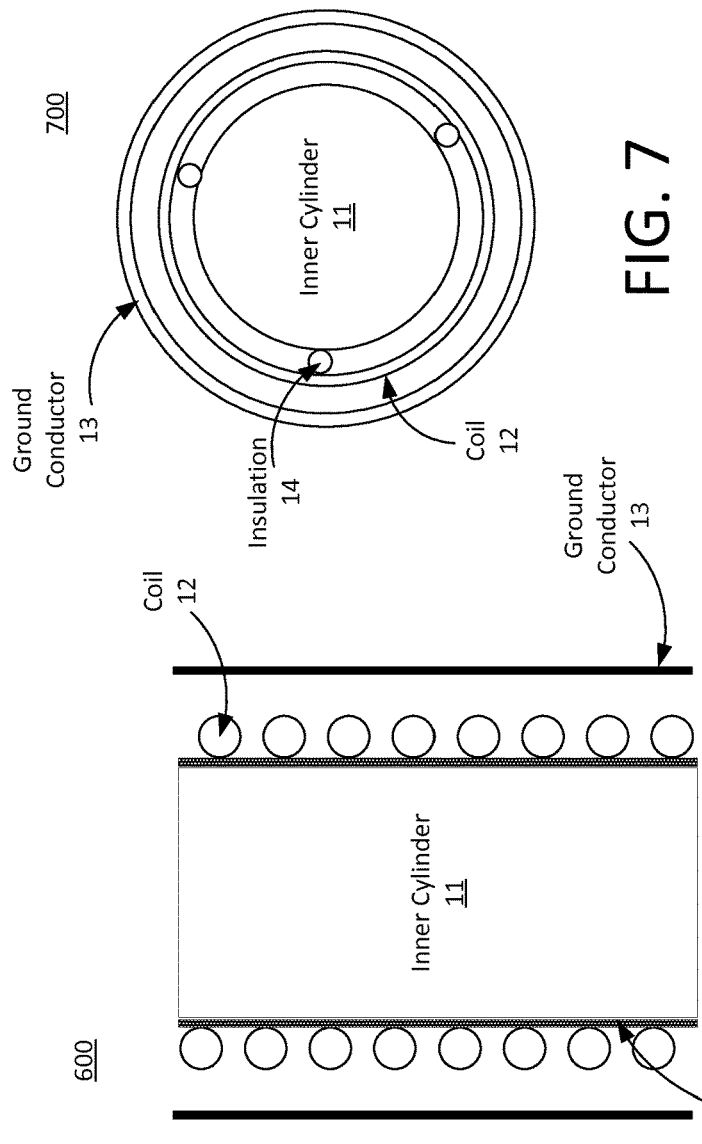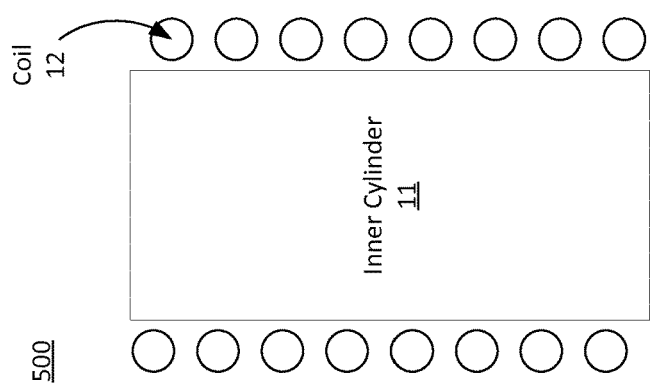

PULSED WAVE GUIDE LIQUID QUALITY MEASUREMENT

RELATED APPLICATIONS

This application claims priority to U.S. Provisional Patent Application No. 62/013,037, filed Jun. 17, 2014 and incorporated by reference herein in its entirety.

FIELD OF THE EMBODIMENTS

Embodiments of the present disclosure relate generally to liquid quality sensors and more particularly to pulsed waveguide liquid quality sensors.

GENERAL BACKGROUND

Knowing the quality of liquid in a tank is useful to a variety of applications. For example, urea-based solutions are often used in automotive application to reduce emissions. In particular, diesel powered motor vehicles include a urea tank, separate from the fuel tank, where the urea tank is used to carry an operating fluid such as an automotive urea solution, or the like. The urea solution is stored in the urea tank and is sprayed into the exhaust gases of the vehicle in order to convert oxides of nitrogen into elementary nitrogen and water. Accordingly, the harmful emissions of the vehicle are reduced. As will be appreciated, various countries in the world have regulated for some vehicles to include urea based emissions systems in order to comply with emissions standards. These systems are sometimes referred to as Selective Catalytic Reduction (SCR) systems or SCR vehicles.

Accordingly, determining the quality of urea in the tank is useful as the quality can affect the operation and effectiveness of an SCR system.

It is with respect to the above the present disclosure is provided.

SUMMARY

Various embodiments of the present disclosure provide a liquid quality measurement system. The quality measurement system may include a pulsed wave guide (PWG) and sensor configured to measure the quality of a liquid based on reflections due to a change in impedance and/or permittivity between the liquid and another medium (e.g., air, another liquid, or the like). Additionally, the system may be configured to measure the quality of a liquid based on a reflection caused by a low impedance path to ground (e.g., caused by grounding the liquid).

In one embodiment, a waveguide system may include an inner core; and a conductor wound around the inner core in conductive coils having a coil length, wherein a voltage pulse received by the pulsed waveguide propagates as an induced wave having a group velocity, the group velocity being below a threshold velocity, wherein a reflection signal or an end of line signal generated within the conductor from the induced wave is detectable from the initial voltage pulse.

In another embodiment, a quality sensing system may include a sensor arranged to transmit an initial voltage pulse; and a waveguide system arranged to receive the initial voltage pulse. The waveguide system may include an inner core; and a conductor wound around the inner core in conductive coils having a coil length, wherein the initial voltage pulse received by the pulsed waveguide propagates as an induced wave having a group velocity, the group velocity being below a threshold velocity, wherein a reflection signal or an end of line signal generated within the conductor from the induced wave is detectable by the sensor from the initial voltage pulse.

In a further embodiment, a method of measuring quality of a liquid may include disposing at least a portion of a waveguide in a liquid, the waveguide system comprising an inner core and a conductor wound around the inner core in conductive coils; receiving an initial voltage pulse in the waveguide, wherein the initial voltage pulse travels along the conductor as a wave; receiving a reflection signal or an end of line signal based upon reflection or propagation of the second wave; and determining a quality of the liquid from the reflection signal or end of line signal.

BRIEF DESCRIPTION OF THE DRAWINGS

FIGS. 5-7 show examples of a PWG;

DESCRIPTION OF EMBODIMENTS

Figure 1:
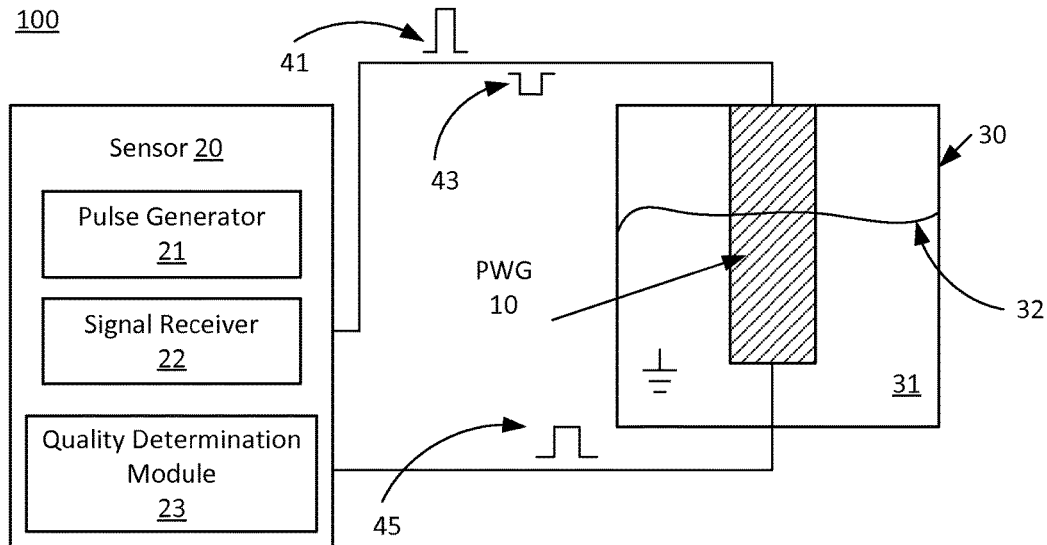
FIGS. 1-3 show a system for measuring a quality of a liquid using a PWG.

Example embodiments will now be described more fully hereinafter with reference to the accompanying drawings, where various embodiments are shown. The present disclosure may be embodied in many different forms and are not to be construed as limited to the examples set forth herein. Rather, these examples are provided so this disclosure will be thorough and complete, and will fully convey the scope of the claims to those skilled in the art. In the drawings, like numbers refer to like elements throughout.

The present disclosure provides a liquid quality sensor, including a waveguide, referred to herein as a "pulsed waveguide" (PWG) having a conductive element. In some examples, at least part of the conductive element is wound in coils around an inner core, such as an inner cylinder. Furthermore, a ground conductor is disposed in the liquid to ground the liquid with respect to the conductive element of the PWG. The PWG is immersed in the liquid and an electric pulse is transmitted to the PWG, wherein the pulse travels along the conductive element as a wave. When the wave encounters a change in medium (e.g., boundary between air and liquid surface, end of the waveguide, or the like) part or all of the energy is reflected and travels back up the coil. The "quality" of the liquid then can be determined based on various characteristics (e.g. polarity, amplitude, phase, or the like) of the reflected wave. In some examples, the wave also travels to the end of the PWG, where an end of line signal or pulse can be realized. The quality can also be determined based on the remaining signal at the end of the PWG.

At least one specific advantage of the present disclosure is the use of wound coil about an inner core in the PWG. In particular, the wound coil ensures the time between an initial pulse and a reflected pulse is significantly slowed due to reduced propagation velocity. As such, simpler and more cost efficient electronics can be employed to generate the initial voltage pulse, detect the reflected pulse, and determine the liquid quality. For example, the present embodiments are compatible for use with commercial electronics that process signals having amplitudes in the range of 10 s of millivolts (mV) at a bandwidth, for example, of 250 mHz, where propagation delay may be in the range of 5 ns. The embodiments are not limited in this context.

Furthermore, the present disclosure may be implemented to measure the quality of a variety of different liquids. Although examples herein discuss measuring the quality of urea, this is done for convenience and clarity and is not intended to be limiting. Furthermore, many of the examples discussed herein discuss determining the quality of the liquid based on the characteristics of a reflected pulse, the quality can also be determined based on the characteristics of an end of line pulse. Examples are not limited in this context and many examples reference the reflected pulse for convenience.

FIG. 1 illustrates a block diagram of a quality sensing system, shown as system 100, arranged in accordance with at least some embodiments of the present disclosure. The system 100 includes a PWG 10 having a wound coil (e.g., refer to FIGS. 5-10) or an equivalent of a wound coil (e.g., refer to FIG. 11) and a sensor 20. The PWG 10 is disposed in a tank 30 having a liquid 31 whose quality (e.g., concentration, level of contamination, or the like) is to be measured by the system 100.

The sensor 20 includes a pulse generator 21, a pulse receiver 22, and quality determination module 23. In general, the sensor 20 is configured to transmit (e.g., with pulse generator 21) an initial pulse 41 to the PWG 10 and receive (e.g., with pulse receiver 22) a reflected pulse 43 back from the PWG 10 as well as an end of line (EOL) pulse, shown as EOL pulse 45, from the PWG 10. The sensor 20 is further configured to determine (e.g., with quality determination module 23) the quality of the liquid 31. In particular, the quality determination module 23 determines the quality of the liquid 31 based on at least some characteristics of the reflected pulse 43 and/or the EOL pulse 45. The quality determination module 23 may include a processor, memory, and associated logic, features, or functionality to determine the amplitude (e.g., refer to reflected pulse amplitude 50 described in conjunction with FIGS. 4A-4B) of the reflected pulse 43 and/or the EOL pulse 45, and the quality (e.g., concentration, or the like) of the liquid 31 based at least on the determined amplitude.

As used herein, liquid "quality" shall mean a quantitative measure of some characteristic(s) of the liquid. For example, with respect to urea, urea solution for selective catalytic reduction applications typically has a concentration of approximately 32.5%+/−5%. As such, in some examples, the quality can be the concentration of the liquid solution (e.g., concentration of urea, or the like).

In general, the quality of liquid 31 can be determined based on the amplitude of the reflected pulse 43. In particular, there is a direct relationship between the conductivity of the liquid and the quality (e.g., the conductivity of a solution and the concentration of urea in the solution, or the like), that is, changes in the conductivity of the liquid 31 may change the amplitude of the reflected pulse 43. As such, the quality of the liquid can be determined based on the amplitude of the reflected pulse 43.

In general, the PWG 10 can be disposed in a variety of locations within the tank 30. For example, as depicted in FIG. 1, the PWG 10 is disposed proximate to the top of the tank 30. As such, the reflected pulse 43 will be created as the initial pulse 41 encounters the liquid surface at level 32. As will be appreciated, the amplitude of the reflected pulse 43 may depend upon the level 32 of the liquid 31 (e.g., due to energy loss, or the like). As such, the quality determination module 23 may determine the quality based on the amplitude of the reflected pulse 43 and the level of the liquid. In further examples, the above-described system for measuring the quality of a liquid can be implemented in conjunction with a system for measuring the level of the liquid.

Figure 2:
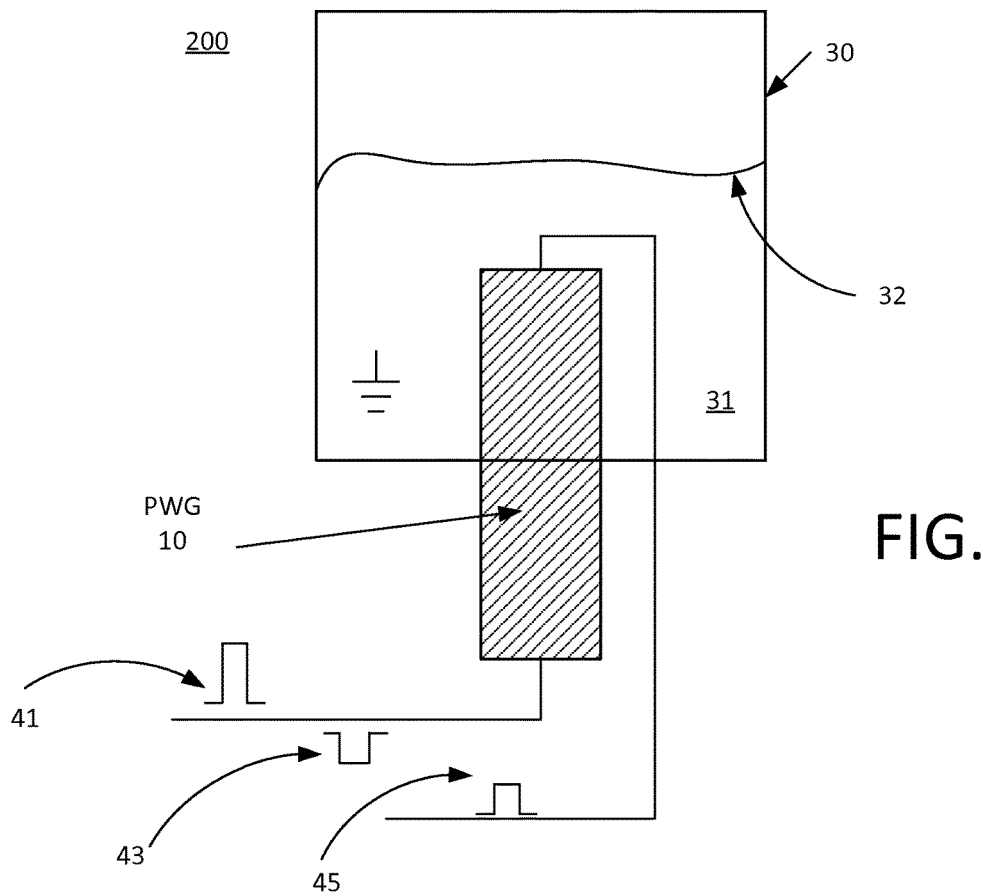

In some examples, the PWG 10 may be disposed at a bottom of the tank 30. For example, FIG. 2 depicts a system 200 wherein the PWG 10 is disposed proximate to a bottom of the tank 30. The reflected pulse 43 is again created when the initial pulse 41 encounters the liquid (e.g., at the bottom of the tank 30). Additionally, the EOL pulse 45 may be received from the end of the PWG 10 as shown. As the PWG 10 extends partially out of the tank 30 and partially in the tank 30, the amplitude of the reflected pulse is not dependent upon the level of the liquid. Specifically, the PWG 10 extends a distance d out of the tank. As this distance d does not change with the level of the liquid 31, the amplitude of the reflected pulse 43 is not dependent upon the level 32. Furthermore, disposing the PWG 10 at the bottom may be advantageous as this location is traditionally the location of an outlet or other location where the liquid 31 is drawn from the tank 30.

Figure 3:
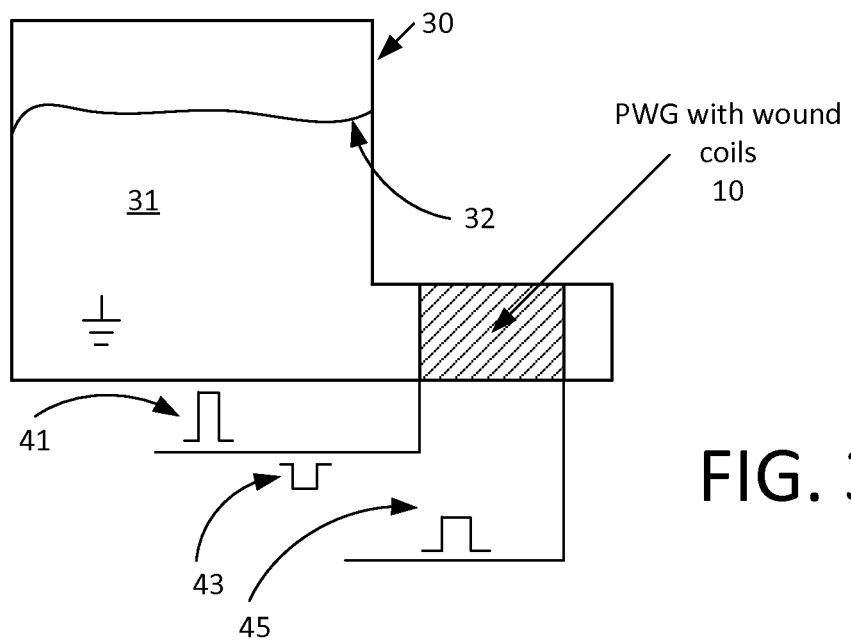

In some examples, the PWG 10 may be disposed in an outlet of the tank 30. For example, FIG. 3 depicts a system 300 wherein the PWG 10 is disposed in an outlet 35 of the tank 30. This may be an ideal location for the PWG 10 in applications where the quality of the liquid may be measured closer to where the liquid is drawn from the tank. The PWG may include an electrical conductor in the form of coils as detailed below with respect to further embodiments. As with the example in FIG. 2, the quality of the liquid (e.g., particularly, the amplitude of the reflected pulse 43) does not depend on the level 32 of the liquid 31.

Figure 4A:
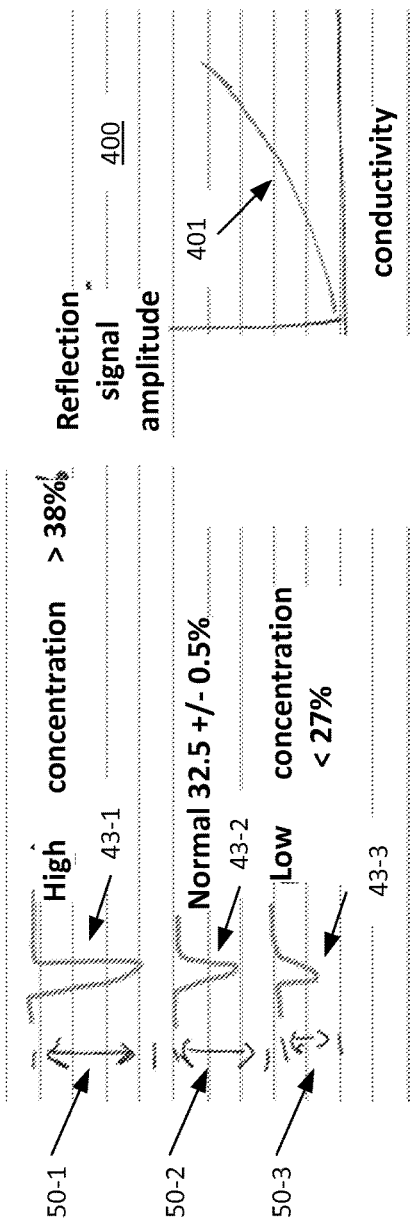
FIGS. 4A-4B show plots associated the amplitude of a reflected pulse and an end of line pulse with liquid quality.

As stated above, the quality of the liquid 31 can be determined based on characteristics of the reflected pulse 43. For example, the amplitude of the reflected pulse 43 can be used to determine the concentration of urea in the liquid 31. In particular, FIG. 4A illustrates a number of example reflected pulses, variants of reflected pulse 43. In particular, example reflected pulses 43-1, 43-2, and 43-3 are depicted. The example reflected pulses 43-1, 43-2, and 43-3 have a corresponding reflected pulse amplitude 50-1, 50-2, and 50-3. The concentration of urea corresponding to a given example reflected pulse can be determined based on this amplitude. In particular, as shown in the plot 400, the concentration of urea can be represented as a function of the reflected pulse amplitude 50. As depicted, the concentration is shown on the x-axis while the reflected pulse amplitude 50 is shown on the y-axis. A function 401 maps the reflected pulse amplitude 50 and the concentration. This function is shown merely as an example and is not intended to be limiting. In particular, the exact function and mapping between amplitude of the reflected pulse and the concentration of the liquid may depend upon the liquid and manufacturing characteristics of the PWG (e.g., coil size, coil diameter, coil pitch, distance to ground, length of the coils, or the like).

As noted, above, the amplitude of an end of line pulse (e.g., refer to FIGS. 1-3 and FIGS. 9-13) can be used to determine the quality of a liquid. The same relationship between amplitude of a reflected pulse and liquid quality explained above can be exploited to determine the liquid quality from the amplitude of an end of line pulse.

Figure 4B:
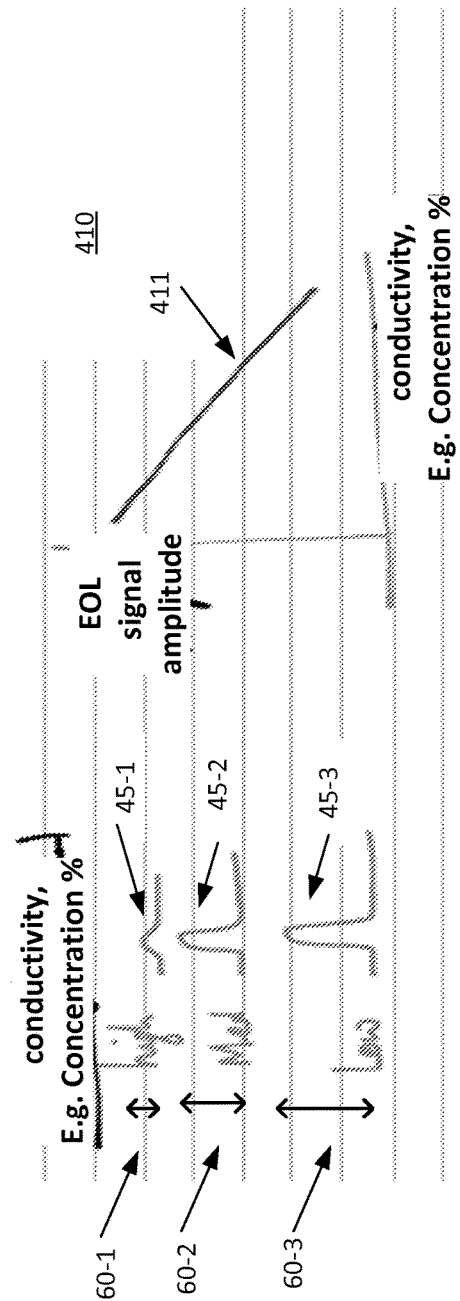

In particular, as depicted in FIG. 4B, the amplitude of the EOL pulse 45 can be correlated to the quality of the liquid as shown by the plotted function. In particular, FIG. 4B illustrates a number of example EOL pulses, variants of EOL pulse 45. In particular, example EOL pulses 45-1, 45-2, and 45-3 are depicted. The example EOL pulses 45-1, 45-2, and 45-3 have a corresponding amplitude 60-1, 60-2, and 60-3. The concentration of urea corresponding to a given example EOL pulse can be determined based on this amplitude. In particular, as shown in the plot 410, the concentration of urea can be represented as a function of the EOL pulse amplitude 60. As depicted, the concentration is shown on the x-axis while the EOL pulse amplitude 60 is shown on the y-axis. A function 411 maps the reflected pulse amplitude 50 and the concentration. This function is shown merely as an example and is not intended to be limiting. In particular, the exact function and mapping between amplitude of the EOL pulse and the concentration of the liquid will depend upon the liquid and manufacturing characteristics of the PWG (e.g., coil size, coil diameter, coil pitch, distance to ground, length of the coils, or the like).

In some embodiments a coil may have a pitch on the order of 0.2 mm to 5 mm and in particular, 3 mm. The embodiments are not limited in this context. Examples of suitable wire gauge include wire having diameter in the range of 0.1 mm to 0.5 mm, for example, 0.5 mm. The embodiments are not limited in this context. The winding diameter of a coil according to some embodiments may vary between 3 mm and 20 mm, for example 5 mm, while the separation of a coil from the inner tube may range between 0.2 mm and 1 mm, for example, 1 mm. By proper choice of these parameters a suitable propagation velocity of a pulse may be generated. For example, in the case of coil pitch of 2 mm, coil wire gauge of 0.5 mm, winding diameter of 5 mm, separation from the outer tube of 2 mm, a propagating velocity of 2 mm per ns is generated. Accordingly, by suitable choice of number of windings in a coil, reflected pulses may be properly detected. For example, for a given pulse width of an initial pulse and a given width of a reflected pulse, a threshold velocity of the pulses for detecting the reflected pulse may be 20 mm/ns. Above this velocity, the reflected pulse may not be readily detected. Accordingly, by providing a coil that generates a propagating velocity (group velocity) for a pulse of 2 mm/ns a reflected pulse may be readily detected and measured by commercially available electronics, as discussed above. This may allow the quality of a liquid to be properly measured by measuring the amplitude of a reflected pulse, for example.

Furthermore, although examples herein use the amplitude of the reflected pulse 43, or EOL pulse 45, other characteristics of the reflected pulse 43 or EOL pulse 45 can be used to determine the liquid quality. For example, the phase of the reflected pulse may be used to determine the liquid quality. For example, while the amplitude of a reflected pulse may indicate the loss due to the conductivity of the liquid, the delay between an initial pulse and reflected pulse may be used as an indication of the dielectric constant and/or the permeability of the liquid. These two parameters influence the propagating velocity of the wave (pulse), hence the delay. In particular embodiments, the duration of an initial pulse may range between 5 ns and 20 ns, and may have a shorter duration or longer duration in other embodiments. A reflected wave (pulse) may inherently be filtered according to the transmission line characteristics of a PWG, resulting in a reflected pulse that may have a Gaussian profile whose duration ranges between approximately 10 ns to 50 ns, and may have an amplitude ranging between 10 mV to 1 V. The embodiments are not limited in this context. In view of the above it may be useful to provide adequate path length within a coil that generates a delay so that a reflected pulse having a width of 30 ns may be properly detected where the velocity of propagation of pulses may be in the range of 2 mm/ns. In particular, the path length, along with the capacitance of the PWG, may be arranged for a reflected pulse, also referred to herein as a reflection signal, to be detected apart from an initial pulse. The delay provided by a PWG of the present embodiments between the generation of an initial pulse, also referred to herein as an initial voltage pulse, and the receipt of the reflected pulse (reflection signal), may be greater than the width of the initial voltage pulse. Thus, for a reflection signal or end-of-line signal to be deemed detectable with respect to an initial voltage pulse, the reflection signal or end-of-line signal is received after the time when the initial voltage pulse is complete.

As indicated above, the PWG 10 includes coils wound about an inner core such as an inner cylinder. Examples of the PWG 10 are shown in FIGS. 5-11. In particular, FIGS. 5-7 show examples of the PWG 10 while FIGS. 8-11 show examples of the PWG 10 inserted into the tank 30. In particular, the following embodiments depict the use of an inner cylinder as an inner core. The present embodiments further include inner cores having other shapes including a rectangular cross section, or other shape.

Turning more specifically to FIG. 5, a cross sectional view of a PWG 500 is shown. The PWG 500 may be implemented in the system 100 as the PWG 10. As depicted, the PWG 500 includes an inner cylinder 11 and an electrical conductor in the form of conductive coils, represented by coils 12, where the coils 12 are wound about the inner cylinder 11. The inner cylinder 11 may comprise a conductive material including steel in various embodiments. The inner cylinder 11 or other inner core may be connected to ground potential, also referred to as electrical ground, in various embodiments. As can be seen, the coils 12 are spaced apart from the inner cylinder 11. During operation, the PWG 500 may be implemented to measure the quality of the liquid 31 based on a reflected wave caused by a change in the dielectric characteristics, the permittivity, or the like between the liquid 31 and the air in the tank.

Turning more specifically to FIG. 6, a cross sectional view of a PWG 600 is shown. The PWG 600 may be implemented in the system 100 as the PWG 10. As depicted, the PWG 600 includes the inner cylinder 11 and the coils 12 wound about the inner cylinder 11. Furthermore, the PWG 600 includes an electrical insulator shown as insulator 14 and disposed between the inner cylinder 11 and the coils 12. In general, the insulation 14 may be configured to space the coils 12 apart from the inner cylinder 11 and to electrically insulate the inner cylinder 11 from the coils 12. Additionally, the PWG 600 includes a ground conductor 13 disposed around the coils 12 and inner cylinder 11. During operation, the PWG 600 may be implemented to measure the liquid quality based on a reflected wave caused by a low impedance path to ground due to the liquid 31 being grounded by the ground conductor 13.

Turning more specifically to FIG. 7, a top view of a PWG 700 is shown. The PWG 700 may be implemented in the system 100 as the PWG 10. As depicted, the PWG 700 includes the inner cylinder 11, insulation 14 disposed around the inner cylinder 11, the coils 12 wound about the insulation 14 and inner cylinder 11, and the ground conductor 13 disposed about the coils 12, the insulation 14 and the inner cylinder 11. In some examples, the insulation 14 may be electrically insulating rods disposed around the inner cylinder 11 as shown. The rods may have a rod axis extending out of the plane of the page. More or less rods than shown may be used. As described above, the insulation 14 may be configured to space the coils and electrically insulate the coils from the inner cylinder. As such, the exact configuration of the insulation can vary.

In various examples, the inner cylinder 11, the coils 12, and ground conductor 13 may be made of material resistant to corrosion by urea.

Figure 8:
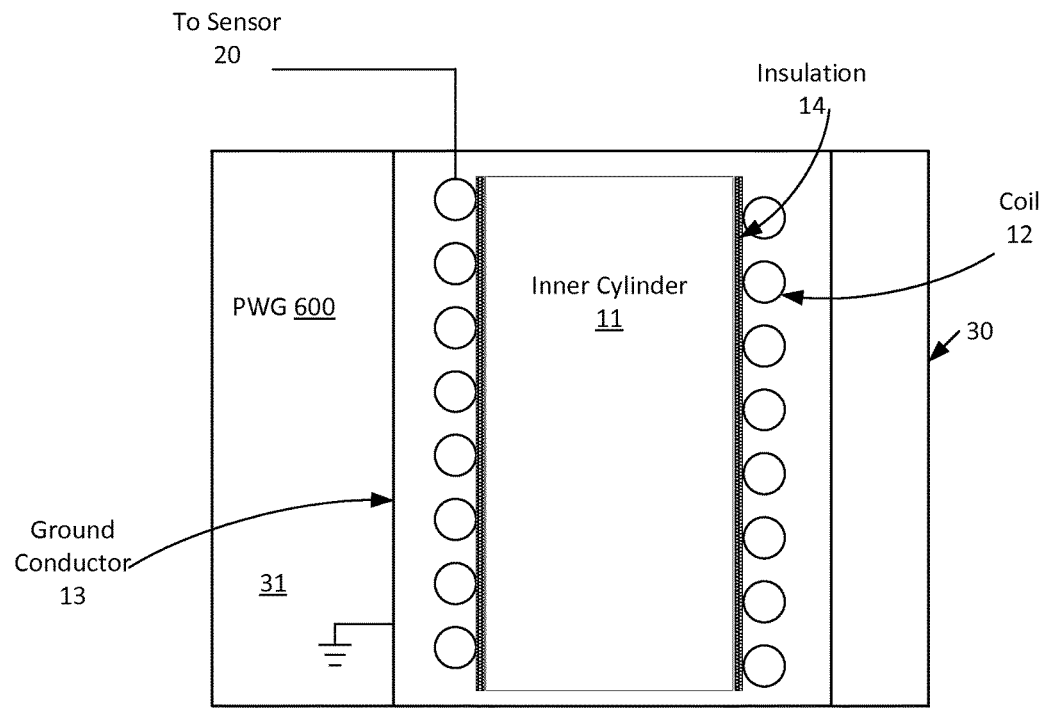
FIGS. 8-12 show example implementations of a PWG in a tank in greater detail.

Turning now to FIGS. 8-11, various configurations of the ground conductor are shown. In particular, FIG. 8 shows a PWG 600 disposed in the tank 30. As can be seen, the coils 12 of the PWG 600 are operably connected to the sensor 20. In particular, the sensor 20 is electrically connected to one end of the coils 12 to communicate voltage pulses (e.g., the initial pulse 41) to the PWG 600 and to receive reflected pulses (e.g., the reflected pulse 43) from the PWG 600. As depicted, the ground conductor 13 is a conductive cylinder (e.g., stainless steel, or the like) disposed around the coils 12. Furthermore, the ground conductor 13 is grounded, and may be referred to as a ground cylinder. As such, the liquid is grounded.

Figure 9:
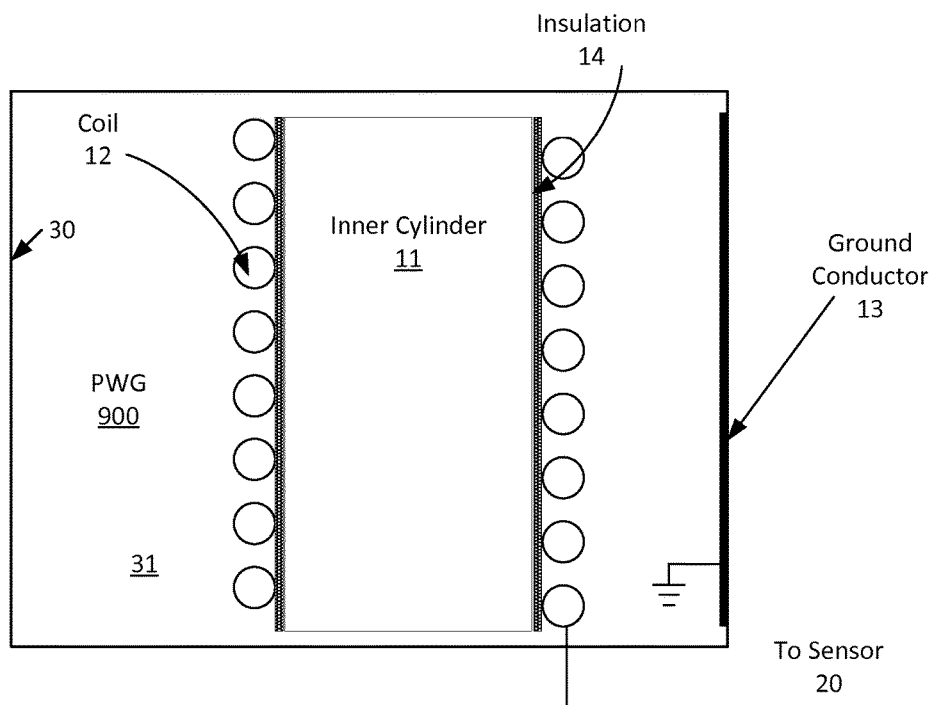

Turning now to FIG. 9, a PWG 900 is shown disposed in the tank 30. As depicted, the PWG 900 is similar to the PWG 600, while the ground conductor 13 is a conductive plate having a plate shape and disposed on a wall of the tank 30 so as to be in contact with the liquid 31. The ground conductor of FIG. 8 may be implemented to provide a consistent distance between the coils 12 and the ground conductor 13. In particular, the grounded liquid creates a low impedance path for the initial pulse 41. An example of a low impedance path is one having an impedance less than 1000 Ohms, and another example is a path having impedance less than 100 Ohms.

During operation, as voltage waves travel through the coils, when the waves encounter the liquid (e.g., the level 32, the bottom of the liquid, or the like) the reflected pulse 43 is created. For example, in some embodiments, the reflected pulse 43 is created due to the change in impedance caused by the grounded liquid being in contact with the coils 12 (e.g., for example using the PWG 600 or 700). As another example, in some embodiments, the reflected pulse 43 is created due to a change in the permittivity or impedance between the air and the liquid 31 (e.g., for example using the PWG 500). In some examples, the reflected pulse 43 is created due to a change in the dielectric characteristics, permittivity, of the liquid 31. In some examples, the reflected pulse 43 is created due to a change in the permeability of the liquid 31.

Figure 10:
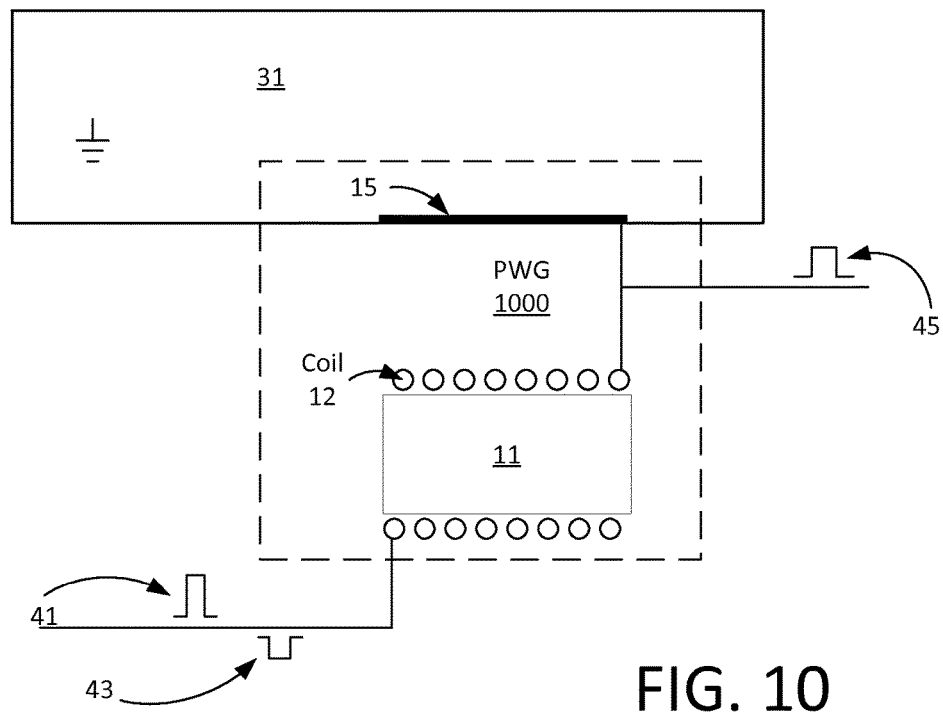

Turning now to FIG. 10, a PWG 1000 is shown disposed in the tank 30. As depicted, the PWG 1000 includes the coils 12 wound about the inner cylinder 11. One end of the coils 12 are electrically connected to the sensor 20 while another end of the coils 12 is electrically connected to an end termination conductor 15 (e.g., conductive plate, conductive wire, or the like). The coils 12 and inner cylinder 11 can be disposed outside the tank 30 while the end termination conductor 15 is disposed inside the tank in contact with the liquid 31. Furthermore, ground conductor 13 is disposed in the tank 30 in contact with the liquid 31. As such, during operation, the reflected pulse is created due to a low impedance path between the ground conductor 13 and the end termination conductor 15.

Figure 11:
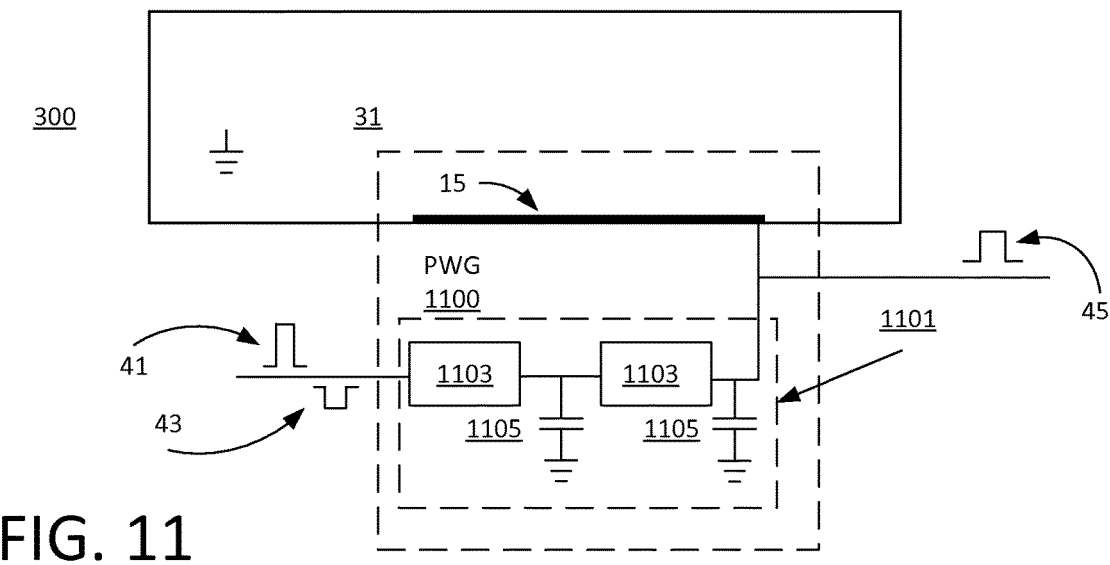

As discussed above, in some examples, an equivalent coil can be used. In particular, an equivalent coil can be implemented in the PWG 10 to "slow" the initial pulse 41 and reflected pulse 43 so sensor 20 can be constructed from simpler and less costly components. FIG. 11 illustrates a PWG 1100 including an equivalent coil 1101. As depicted, the PWG 1100 includes the equivalent coil 1101. The equivalent coil 1101 is electrically connected between the sensor 20 and the end termination conductor 15, disposed in the tank 30 as discussed above in conjunction with FIG. 10. During operation, the equivalent coil 1101 operates to slow the initial pulse 41 and reflected pulse 43. In some examples, the equivalent coil 1101 can be constructed from two LC circuits. In particular, the equivalent coil 1101 can be made from two inductors 1103 electrically connected series with capacitors 1105 electrically connected between ground and either side of the second inductor, as illustrated. In other words, the equivalent coil comprising a first inductor and a second inductor, a first capacitor disposed in electrical series between the first inductor and second inductor, and a second capacitor disposed in electrical series with the first inductor, second inductor, and first capacitor.

Figure 12:
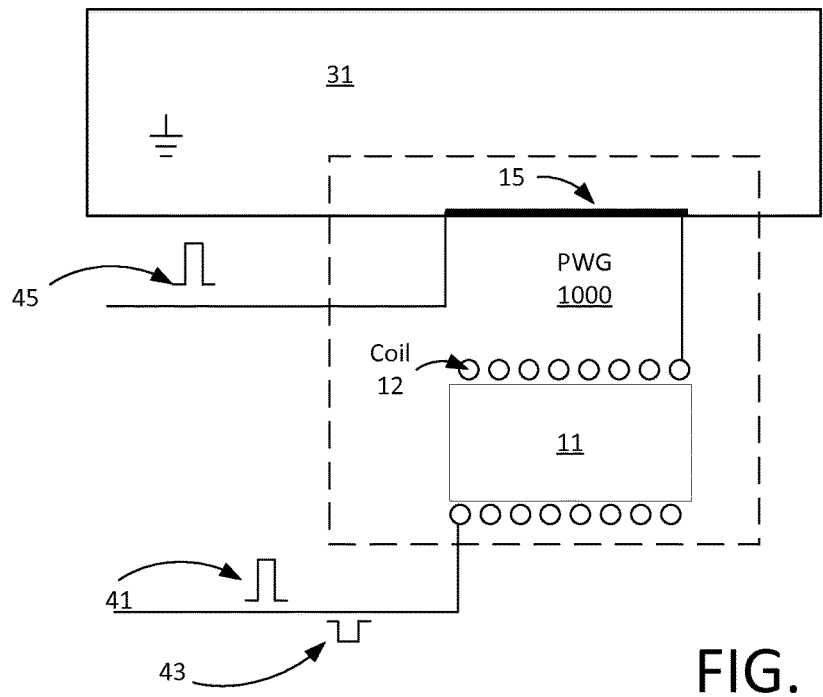

FIG. 12 depicts the PWG 1000 described above in conjunction with FIG. 10. The PWG 1000 operates as described above. Additionally, an EOL pulse 45 can be captured from the end of the end termination conductor 15. As noted above, the liquid quality can be determined based on the amplitude of the EOL pulse 45 and/or the reflected pulse 43. As such, the system shown in FIG. 12 may be implemented to determine liquid quality based on either or both of the reflected pulse 43 and the EOL pulse 45. Any of the other PWGs described herein can be implemented so the sensor 20 can receive the end of line pulse, EOL pulse 45, and use the received end of line pulse to determine liquid quality.

Furthermore, in some examples, the coils 12 and/or the end termination conductor 15 may be coated with a resistive coating. As such, when waves traveling through the PWG encounter a low impedance path to ground, or a change in the dielectric characteristics or permittivity of the surrounding medium (e.g., air, liquid 31, or the like) at least a portion of the wave may continue to travel to the end of the PWG. This may be advantageous in instances where the EOL pulse 45 is used to determine the liquid quality surface, and/or to compensate for variations of measurement due to temperature or other environmental factors.

Similarly, the coil 12 can be totally insulated from the liquid to prevent long-term degradation of the contact surface. In this example, as described above, the reflected pulse (e.g., reflected pulse 43) is generated due to change in characteristic impedance of the surrounding medium (e.g., liquid 31.)

Figure 13:
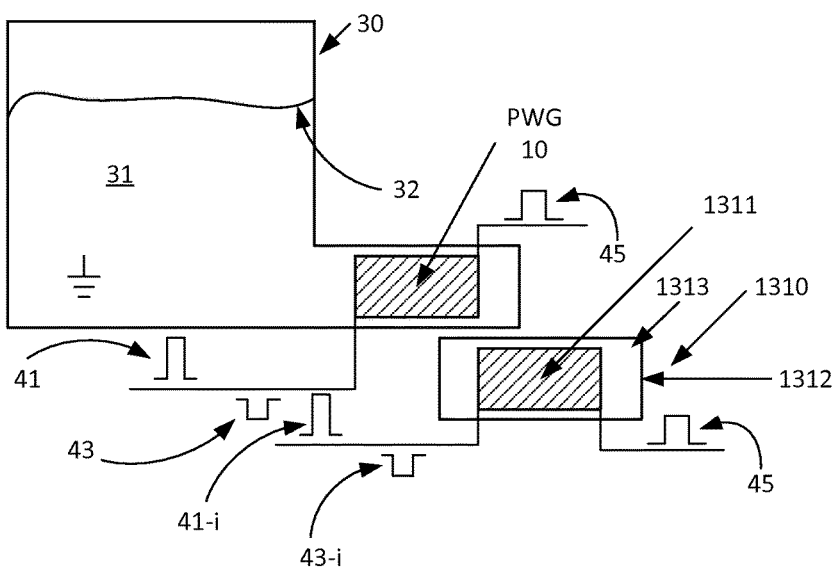
FIG. 13 shows an example including a control for measuring quality of a liquid using radiometric measurements.

FIG. 13 depicts a system 1300 including a PWG 10 configured to measure the quality of a liquid as described above. Furthermore, the system 1300 includes a reference measurement component 1310 including a second PWG 1311 disposed in a sealed container 1312. The sealed container 1312 includes a second liquid, referred to herein as an ideal liquid 1313. The ideal liquid 1313 may have predetermined properties, such as an ideal liquid quality the first liquid, liquid 31, is being compared against. The PWG 10 and second PWG 1311 may operate as the other PWGs described herein. In other words, the second PWG 1311 may have identical construction as the PWG 10. In response to a second initial pulse 41-$i$ the second PWG 1311 may generate a second reflected pulse 43-$i$ or second end of line pulse 45$i$ used to determine the quality of the liquid 31 based on various measurements. In some examples, the system 1300 may be implemented to compensate for effects on the sensor caused by environmental conditions (e.g., temperature, or the like). As illustrated the reference measurement component 1310 may be disposed adjacent the PWG 10.

In operation in a location such as a motor vehicle, the system 1300 may undergo changes in ambient conditions including changes in temperature. By providing the reference measurement component 1310, changes in signals in the PWG caused by changes in ambient conditions may be adjusted as described below. For example, in different implementations, a first operation may involve generating an initial voltage pulse. The initial voltage pulse may be separate initial voltage pulses as shown in FIG. 13, or may be a single initial voltage pulse that is sent to both PWG 10 and second PWG 1311. Subsequently a sensor such as sensor 20 may perform a first operation of detecting a first reflection signal or first end-of-line signal in the first waveguide, PWG 10, based upon the initial voltage pulse. The sensor 20 may perform a second operation of detecting a second reflection signal or second end-of-line signal in the second waveguide based upon the initial voltage pulse.

For a given initial voltage pulse, when the temperature in the ambient of system 1300 increases from a first temperature to a second temperature, the amplitude or other characteristic of a signal detected at the second temperature may vary from the amplitude or other characteristic of a signal detected at the first temperature. Accordingly, the sensor 20 may perform the further operation of determining a quality of the first liquid in tank 30 by comparing the second reflection signal or second end-of-line signal to the first reflection signal or first end-of-line signal. For example, since the reference measurement component 1310 includes an ideal liquid, the amplitude of a received reflection signal from PWG 1311 may be characteristic of the ideal liquid at the second temperature. Accordingly, if the amplitude of a received reflection signal from PWG 10 varies from the amplitude of the reflection signal of PWG 1311, the difference in amplitude may be attributable to a difference in quality of liquid in tank 30 from the ideal liquid.

Figure 14:
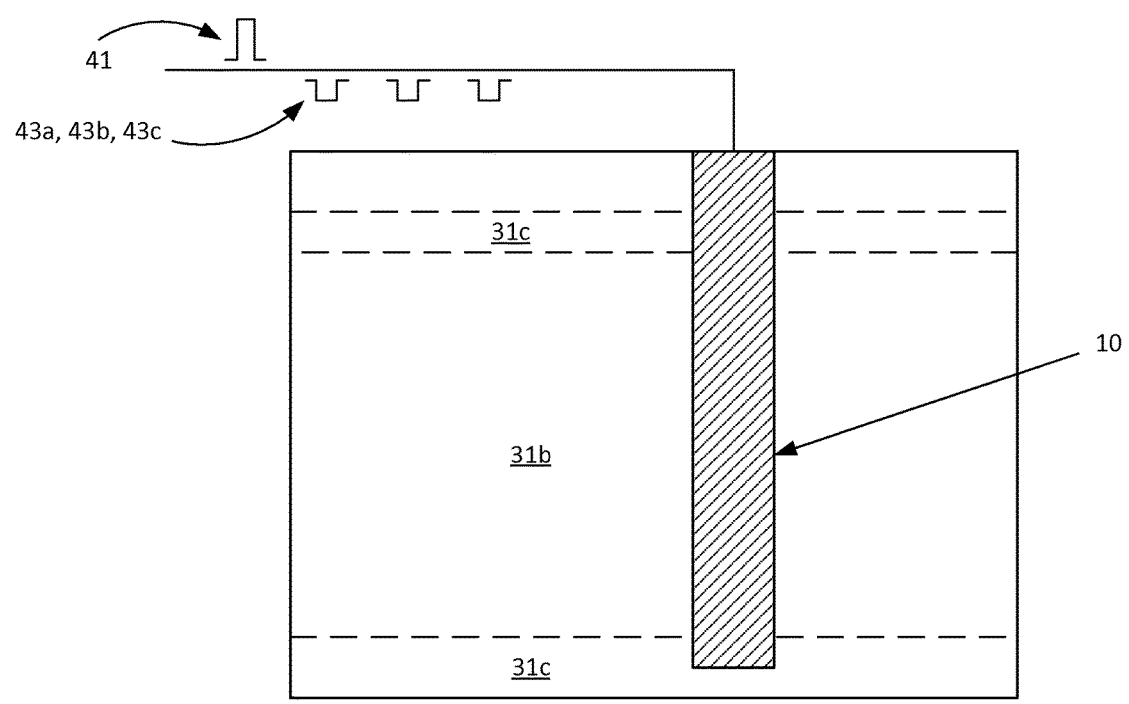
FIG. 14 shows an example of reflected pulses from a PWG in contaminated liquid, arranged according to at least some embodiments of the present disclosure.

FIG. 14 depicts a series of reflected pulses 43a, 43b, and 43c. The reflected pulses 43a, 43b, 43c may be created by contaminated liquid. For example, FIG. 14 shows the tank 30 with PWG 10 disposed therein. Furthermore liquid 31a, 31b, and 31c, may be the liquid intended plus contaminant liquids, where the various liquids form a plurality of layers. A reflection may be created at the boundary between air and the liquid 31a, and the boundary between liquids 31a/31b and at the boundary between liquids 31b/31c. The amplitude of these reflections can vary. Furthermore, the sensor 20 can determine the level of contamination of the liquid 31 based on the number of reflections, the presence of more than 1 reflection, or the amplitude of the reflections.

While the present disclosure has been disclosed with reference to certain embodiments, numerous modifications, alterations and changes to the described embodiments are possible while not departing from the sphere and scope of the present embodiments, as defined in the appended claims. Accordingly, the following claims are intended not to be limited to the described embodiments, and are to be given the full scope defined by the language of the claims, and any equivalents thereof.

What is claimed is:

1. A pulsed waveguide, comprising: an inner core; a conductor wound around the inner core in conductive coils having a coil length, a pitch in a range of 0.2 mm to 5 mm, and the coils having a diameter of 0.1 to 5 mm, wherein an initial voltage pulse received by the pulsed waveguide propagates as an induced wave having a group velocity, the group velocity being below a threshold velocity and having a value in a range of 2 mm/ns up to 20 nm/ns, wherein a reflection signal or an end of line signal generated within the conductor from the induced wave is detectable from the initial voltage pulse; and an electrical insulator disposed between the inner core and conductor, the electrical insulator configured to space the conductor apart from the inner core.

2. The pulsed waveguide of claim 1, wherein the inner core comprises an electrical conductor.

3. The pulsed waveguide of claim 1, wherein the electrical insulator comprises a plurality of rods having a rod axis parallel to an axis of the inner core.

4. The pulsed waveguide of claim 1, further comprising a ground conductor connected to electrical ground and having a plate shape, the ground conductor being spaced from the conductor.

5. The pulsed waveguide of claim 1, wherein the conductor comprises a first end configured to receive the voltage pulse and a second end, the waveguide further comprising an end termination conductor electrically connected to the second end.

6. The pulsed waveguide of claim 1, wherein the inner core and conductor comprise a first waveguide, the pulsed waveguide further comprising a reference measurement component, the reference measurement component including a sealed container, a second waveguide disposed in the sealed container, and a liquid having predetermined properties disposed within the sealed container, the second waveguide having identical construction as the first waveguide, wherein the reference measurement component is disposed adjacent the first waveguide.

7. The pulsed waveguide of claim 1, further comprising a ground cylinder disposed around the inner core.

8. The pulsed waveguide of claim 7, wherein the inner core, ground cylinder, and conductor comprise stainless steel.

9. A quality sensing system, comprising: a sensor arranged to transmit an initial voltage pulse; and a pulsed waveguide arranged to receive the initial voltage pulse, the pulsed waveguide comprising: an inner core; a conductor wound around the inner core in conductive coils having a coil length, a pitch in a range of 0.2 mm to 5 mm, and a diameter of 0.1 to 5 mm, wherein the initial voltage pulse received by the pulsed waveguide propagates as an induced wave having a group velocity, the group velocity being below a threshold velocity and having a value in a range of 2 mm/ns up to 20 nm/ns, wherein a reflection signal or an end of line signal generated within the conductor from the induced wave is detectable by the sensor; and an electrical insulator disposed between the inner core and conductor, the electrical insulator configured to space the conductor apart from the inner core.

10. The quality sensing system of claim 9, further comprising a tank to contain a liquid, wherein at least a portion of the waveguide is in contact with the liquid.

11. The quality sensing system of claim 10, wherein the sensor comprises:
a pulse generator to generate the initial voltage pulse;
a pulse receiver to receive the reflection signal or end of line signal; and
a quality determination module to determine a quality of the liquid based upon a characteristic of the reflection signal or end of line signal, wherein the characteristic comprises an amplitude, phase, or polarity.

* * * * *